United States Patent
Bagge et al.

(10) Patent No.: US 10,571,436 B2
(45) Date of Patent: Feb. 25, 2020

(54) TRANSDUCER ARRAY CMUT ELEMENT BIASING

(71) Applicant: B-K Medical Aps, Herlev (DK)

(72) Inventors: Jan P. Bagge, Stenlose (DK); Lars N Moesner, Glostrup (DK); Henrik Jensen, Bagsvaerd (DK)

(73) Assignee: B-K Medical Aps, Herlev (DK)

(*) Notice: Subject to any disclaimer, the term of this patent is extended or adjusted under 35 U.S.C. 154(b) by 413 days.

(21) Appl. No.: 15/506,094

(22) PCT Filed: Aug. 25, 2014

(86) PCT No.: PCT/IB2014/064055
§ 371 (c)(1),
(2) Date: Feb. 23, 2017

(87) PCT Pub. No.: WO2016/030717
PCT Pub. Date: Mar. 3, 2016

(65) Prior Publication Data
US 2017/0269039 A1    Sep. 21, 2017

(51) Int. Cl.
*G01N 29/24* (2006.01)
*G01H 11/06* (2006.01)
(Continued)

(52) U.S. Cl.
CPC ........... *G01N 29/24* (2013.01); *A61B 8/4444* (2013.01); *B06B 1/0292* (2013.01); *G01H 11/06* (2013.01);
(Continued)

(58) Field of Classification Search
CPC ............... G01N 29/24; G01N 29/2406; G01N 2291/106; H01L 21/28; G01H 11/06; A61B 8/4444; A61B 2562/028; B06B 1/0292
See application file for complete search history.

(56) References Cited

U.S. PATENT DOCUMENTS

| 8,315,125 B2 | 11/2012 | Lemmerhirt |
| 2003/0048698 A1 | 3/2003 | Barnes et al. |

(Continued)

FOREIGN PATENT DOCUMENTS

WO    WO-2016030717 A1 *   3/2016   ......... G01N 29/2406

OTHER PUBLICATIONS

International Search Report for PCT/IB2014/064055 published as WO2016/030717 A1 dated Mar. 3, 2016.
(Continued)

*Primary Examiner* — Daniel Pihulic

(74) *Attorney, Agent, or Firm* — Anthony M. Del Zoppo, III; Daugherty & Del Zoppo Co. LPA

(57) ABSTRACT

An apparatus includes a transducer array with a plurality of CMUT elements. Each of the plurality of CMUT elements includes a first end and a second end. The transducer array further includes a bias network that is electrically connected with the first and second ends of the plurality of CMUT elements. The bias network applies a first bias voltage to the first end of the plurality of CMUT elements and a second bias voltage to the second end of the plurality of CMUT elements. The first and second bias voltages bias the plurality of CMUT elements. A method includes biasing, with bias network, a CMUT element of an transducer array using a bipolar signal that includes a first bias voltage and a second bias voltage, transmitting, by a transmit circuit, a transmit signal to the CMUT element, receiving, by a receive circuit, a receive signal from the CMUT element.

20 Claims, 7 Drawing Sheets

(51) Int. Cl.
  *A61B 8/00* (2006.01)
  *H01L 21/28* (2006.01)
  *B06B 1/02* (2006.01)

(52) U.S. Cl.
  CPC ........ *H01L 21/28* (2013.01); *A61B 2562/028* (2013.01); *G01N 2291/106* (2013.01)

(56) References Cited

U.S. PATENT DOCUMENTS

| | | |
|---|---|---|
| 2005/0119575 A1 | 6/2005 | Ladabaum et al. |
| 2007/0079658 A1* | 4/2007 | Wagner ................ B06B 1/0207 73/627 |
| 2009/0251025 A1 | 10/2009 | Kondou et al. |
| 2010/0063397 A1 | 3/2010 | Wagner |
| 2010/0278015 A1 | 11/2010 | Huang |
| 2017/0269039 A1* | 9/2017 | Bagge ................ G01N 29/2406 |

OTHER PUBLICATIONS

Parisa Behnamfar et al., A CMUT read-out circuit with improved receive sensitivity using an adaptive biasing technique, Biomedical Circuits and Systems Conference, 2011 IEEE Nov. 10, 2011.

Savoia et al., A CMUT Probe for Medical Ultrasonography: From Microfabrication to System Integration, IEEE Transactions on Ultrasonics, Ferroelectrics, and Frequency Control, vol. 59, No. 6, Jun. 2012.

\* cited by examiner

TRANSDUCER ARRAY CMUT ELEMENT BIASING

RELATED APPLICATION

This application is a national filing of PCT application Serial No. PCT/IB2014/064055, filed Aug. 25, 2014, published as WO2016/030717 on Mar. 3, 2016. This application claims priority to PCT application Serial No. PCT/IB2014/064055, published as WO2016/030717 on Mar. 3, 2016.

TECHNICAL FIELD

The following generally relates to ultrasound (US) and more particularly to biasing a Capacitive Micro-machined Ultrasound Transducer (CMUT) element of a transducer array, and is described with particular application to ultrasound imaging.

BACKGROUND

Ultrasound imaging has provided useful information about the interior characteristics of an object or subject under examination. An ultrasound scanner has included a transducer array with transducer elements that transmit ultrasonic waves into a field of view and that receive echoes reflected from structure in the field of view. The echoes are processed, generating an image of the structure and field of view. Transducer elements include a piezoelectric transducer (PZT) element, a ceramic element, and Capacitive Micro-machined Ultrasound Transducer (CMUT) element.

With a CMUT element, energy transduction in receive mode corresponds to a change in capacitance of a capacitive element therein. For transmit, a suitable applied bias voltage causes electrostatic forces that vibrate the capacitive element, which produces ultrasonic waves. For receive, echoes incidence on the capacitive element modulate the capacitance of the capacitive element, invoking generation of a corresponding voltage. For transmit and receive, a high bias voltage will result in a high sensitivity/conversion efficiency. FIGS. 1 and 2 illustrated two different prior art biasing approaches.

FIG. 1 depicts front end electronics $102_1, \ldots, 102_N$ for a CMUT element $104_1, \ldots, 104_N$, where N is a positive integer. Each front end includes a transmit channel $106_1, \ldots, 106_N$ and a receive channel $108_1, \ldots, 108_N$. The transmit channel $106_1, \ldots, 106_N$ include an anti-pole diode $110_1, \ldots, 110_N$ that passes a high voltage transmit pulse from transmit circuitry (TX) during transmit and acts as an open circuit during receive. Each front end further includes an amplifier $112_1, \ldots, 112_N$ that amplifies and routes CMUT element signals to receive circuitry (RX) during receive. The amplifier $112_1, \ldots, 112_N$ is referenced to ground 122 through resistive element $124_1, \ldots, 124_N$. The transmit signal can also be referenced to ground 122. The input signal is maintained below ±0.6V for the amplifier $112_1, \ldots, 112_N$ to function properly.

A bias-network $114_1, \ldots, 114_N$ includes a resistive element $116_1, \ldots, 116_N$ and a CMUT element $104_1, \ldots, 104_N$, arranged as an RC network, or a low pass filter. The resistive element $116_1, \ldots 116_N$ isolates the CMUT element $104_1, \ldots, 104_N$ from a bias voltage 120 at the working frequency, while allowing the bias voltage 120 to charge the CMUT element $104_1, \ldots, 104_N$ to the DC bias potential. A DC-blocking capacitor $118_1, \ldots, 118_N$ is located between both the CMUT element $104_1, \ldots, 104_N$ and the amplifier $112_1, \ldots, 112_N$ and the anti-pole diode $110_1, \ldots, 110_N$. The bias voltage 120 is applied to each bias-network $114_1, \ldots, 114_N$, and each CMUT element $104_1, \ldots, 104_N$ is electrically connected to a same electrical ground 122.

The sensitivity/conversion efficiency of the CMUT element $104_1, \ldots, 104_N$ can be increased by increasing the bias voltage 120. However, generally, the resistive element $116_1, \ldots, 116_N$ and the capacitive element $118_1, \ldots, 118_N$ are electrically rated for the bias voltage 120. As such, in order to increase the sensitivity/conversion efficiency through increasing the bias voltage, the resistive element $116_1, \ldots, 116_N$ and the capacitive element $118_1, \ldots, 118_N$ would need to be higher rated components, which may add cost and physical space.

FIG. 2 is similar except the bias-network $114_1, \ldots, 114_N$ is omitted, the bias voltage 120 is directly connected to the CMUT $104_1, \ldots, 104_N$, and the CMUT $104_1, \ldots, 104_N$ is directly connected to the amplifier $112_1, \ldots, 112_N$. Unfortunately, a fault in a single CMUT element $104_1, \ldots, 104_N$ will apply the full bias voltage 120 to the amplifier $112_1, \ldots, 112_N$ (an electrical short), which can damage circuitry of the scanner, or fault the bias voltage 120 (an open circuit), which may fault the entire transducer. This configuration may also require a very low noise bias voltage, as there is no filtering performance of a bias resistive element like the resistive element $116_1, \ldots, 116_N$.

SUMMARY

Aspects of the application address the above matters, and others.

In one aspect, an apparatus includes a transducer array with a plurality of CMUT elements. Each of the plurality of CMUT elements includes a first end and a second end. The transducer array further includes a bias network that is electrically connected with the first and second ends of the plurality of CMUT elements. The bias network applies a first bias voltage to the first end of the plurality of CMUT elements and a second bias voltage to the second end of the plurality of CMUT elements. The first and second bias voltages bias the plurality of CMUT elements.

A method includes biasing, with bias network, a CMUT element of an transducer array using a bipolar signal that includes a first bias voltage and a second bias voltage, transmitting, by a transmit circuit, a transmit signal to the CMUT element, receiving, by a receive circuit, a receive signal from the CMUT element.

In another aspect, an ultrasound imaging system includes at least one transducer element and a bias network of the at least one transducer element. The bias network is configured to provide bipolar biasing for the at least one transducer element.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
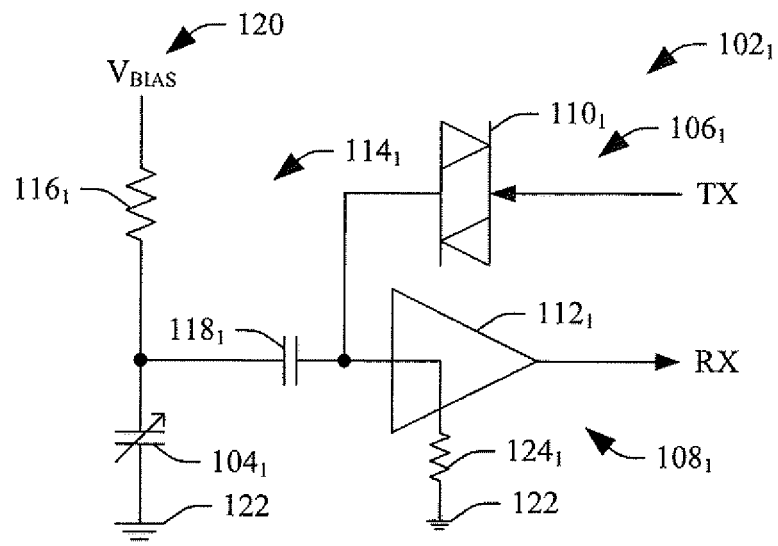
FIG. 1 shows prior art a CMUT element biasing approach.
Figure 1:
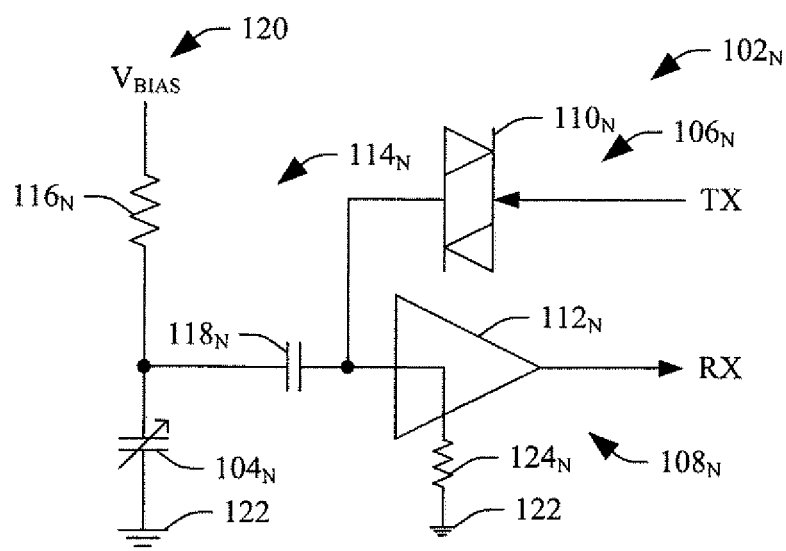
Figure 2:
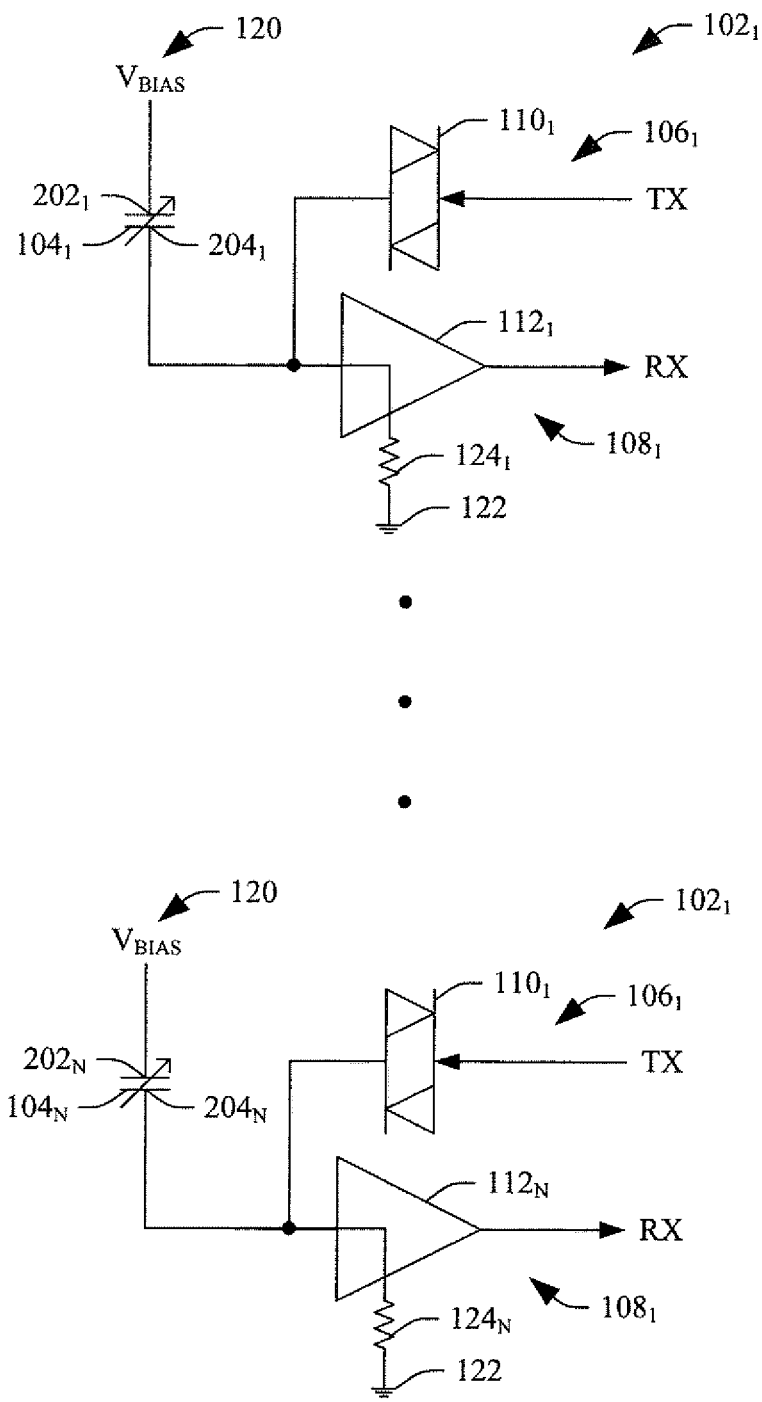
FIG. 2 shows another prior art CMUT element biasing approach.
Figure 3:
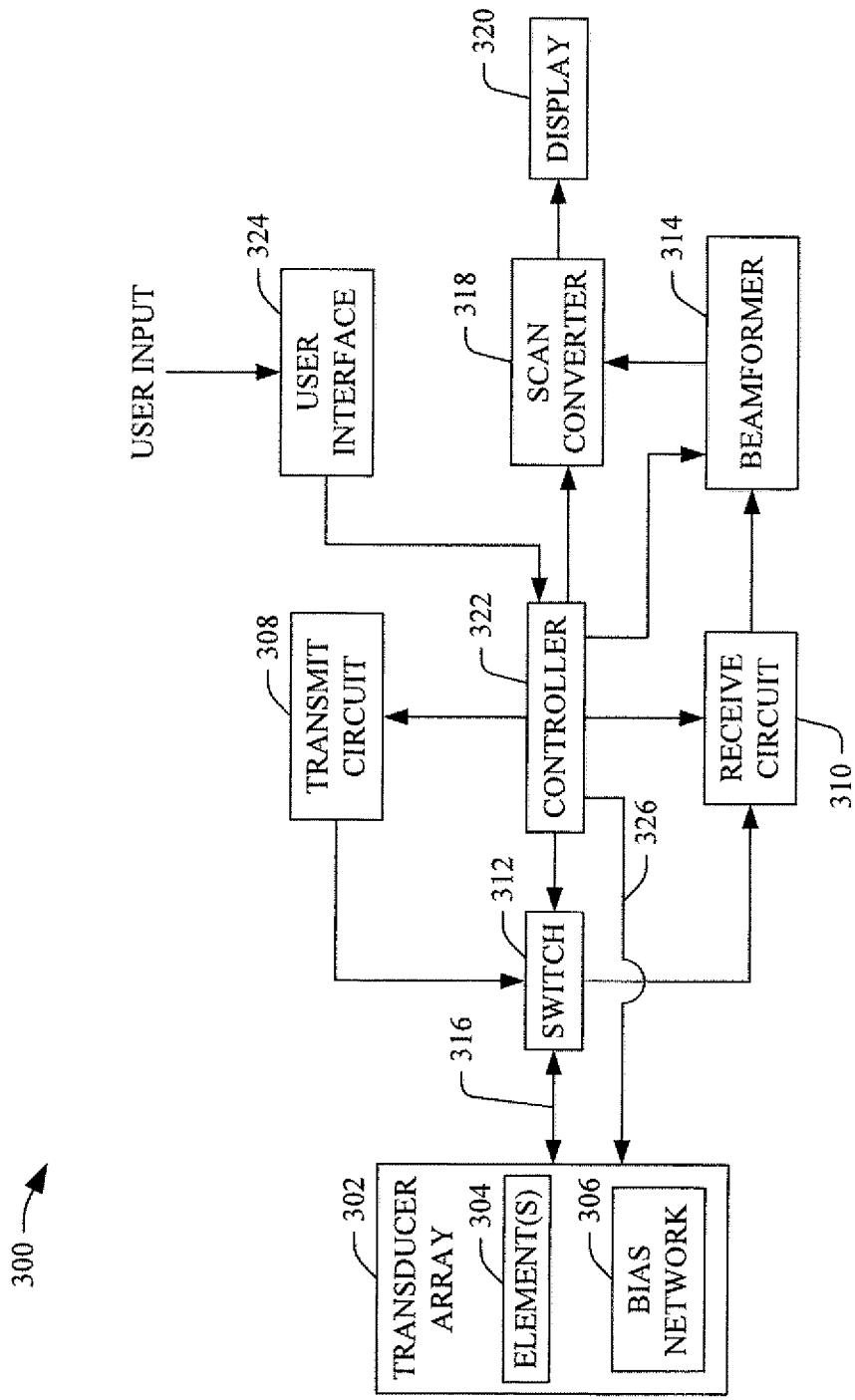
FIG. 3 schematically illustrates an ultrasound imaging system with an array of CMUT elements and a CMUT element bias network.

FIG. 3 illustrates an apparatus 300 such as imaging system, e.g., an ultrasound imaging system. The apparatus 300 includes at least one 1D or 2D transducer array 302 with one or more (e.g., N=32, 64, 128, 192, 256, etc.) transducer elements 304. In one instance, the transducer array 302 includes only CMUT elements 304. In another instance, the transducer array 302 includes CMUT elements 304 and at least one non-CMUT element 304. The transducer array 304 may be linear and/or curved, and/or full or sparse, and can be employed to acquire data for A-mode, B-mode, etc. acquisitions.

The transducer array 302 further includes a bias network 306 for biasing the CMUT elements 304. As described in greater detail below, the bias network 306 supplies a bias voltage to the electrical ground of the CMUT elements 304 that is greater (e.g., 1.5, 2.0, 4.0, etc. times) than a bias voltage applied to the resistive and capacitive components of the bias network 306. In one instance, this allows for increasing the sensitivity/conversion efficiency of the CMUT elements 304, by increasing the voltage across the CMUT elements 304, while maintaining the voltage across the resistive and capacitive components and using the same rated resistive and capacitive components, which can mitigate added cost and space. Furthermore, the bias network 306 limits the operating voltage to a safe level for the apparatus 300.

The apparatus 300 further includes a transmit circuit 308 that transmits a signal (e.g., a voltage pulse) that excites the CMUT elements 304 to emit or transmit ultrasonic waves that traverse a field of view. The transmit circuit 308 also controls phasing and/or time of actuation of each of the CMUT elements 304, which allows for steering and/or focusing a transmitted beam. The apparatus 300 further includes a receive circuit 310 that at least routes signals generated by and from the CMUT elements 304 for processing. The apparatus 300 further includes a switch 312 that switches between the transmit circuit 310 and the receive circuit 310 for transmit and receive operations using an electrical path 316.

The apparatus 300 further includes a beamformer 314. For B-mode imaging and other applications, the beamformer 314 beamforms (e.g., delays and sums) the signals from the CMUT elements 304 into a sequence of focused, coherent echo samples along focused scanlines of a scanplane. The beamformer 314 (and/or other circuitry) may also be configured to variously process the scanlines, e.g., to lower speckle and/or improve specular reflector delineation via spatial compounding and/or other processing such as FIR filtering, IIR filter, etc.

The apparatus 300 further includes a scan converter 318 and a display 320. In one instance, the scan converter 318 converts the scanlines to generate data for display, for example, by converting the scanlines to the coordinate system of the display 320, which displays the scanplane. The converting may include changing the vertical and/or horizontal scan frequency of signal based on the display 320.

The scan converter 318 can be configured to employ an analog scan converting approach and/or a digital scan converting approach.

The apparatus 300 further includes a controller 322 that controls at least one of the transmit circuit 308, the receive circuit 310, the switch 312, the beamformer 314, and/or the scan converter 318. The controller 322 may include a microprocessor, a central processing unit, or the like. Such control may include controlling one or more of the bias voltages of the bias network 306. This may include adjusting or changing one of the bias voltages in connection with a mode of operation, a selected imaging protocol, a CMUT sensitivity/conversion efficiency of interest, etc. In the illustrated embodiment, such a control signal can be conveyed over a control path 326 and/or otherwise to the transducer elements 304.

The apparatus 300 further includes user interface 324, which includes an input device and/or an output device for interacting with the controller 322. The input device 324 may include buttons, knobs, a touch screen, etc., and the output device may include visual (e.g., LCD, LED, etc.) and/or audible displays. In one instance, the user interface 324 allows a user of the apparatus 300 to interact with the apparatus 300. An example of such interaction includes selecting and/or adjusting a sensitivity/conversion efficiency of the CMUT elements 304, which, as discussed herein, can be set by setting/adjusting the bias voltage across the bias network 306 and/or the CMUT elements 304.

Figure 4:
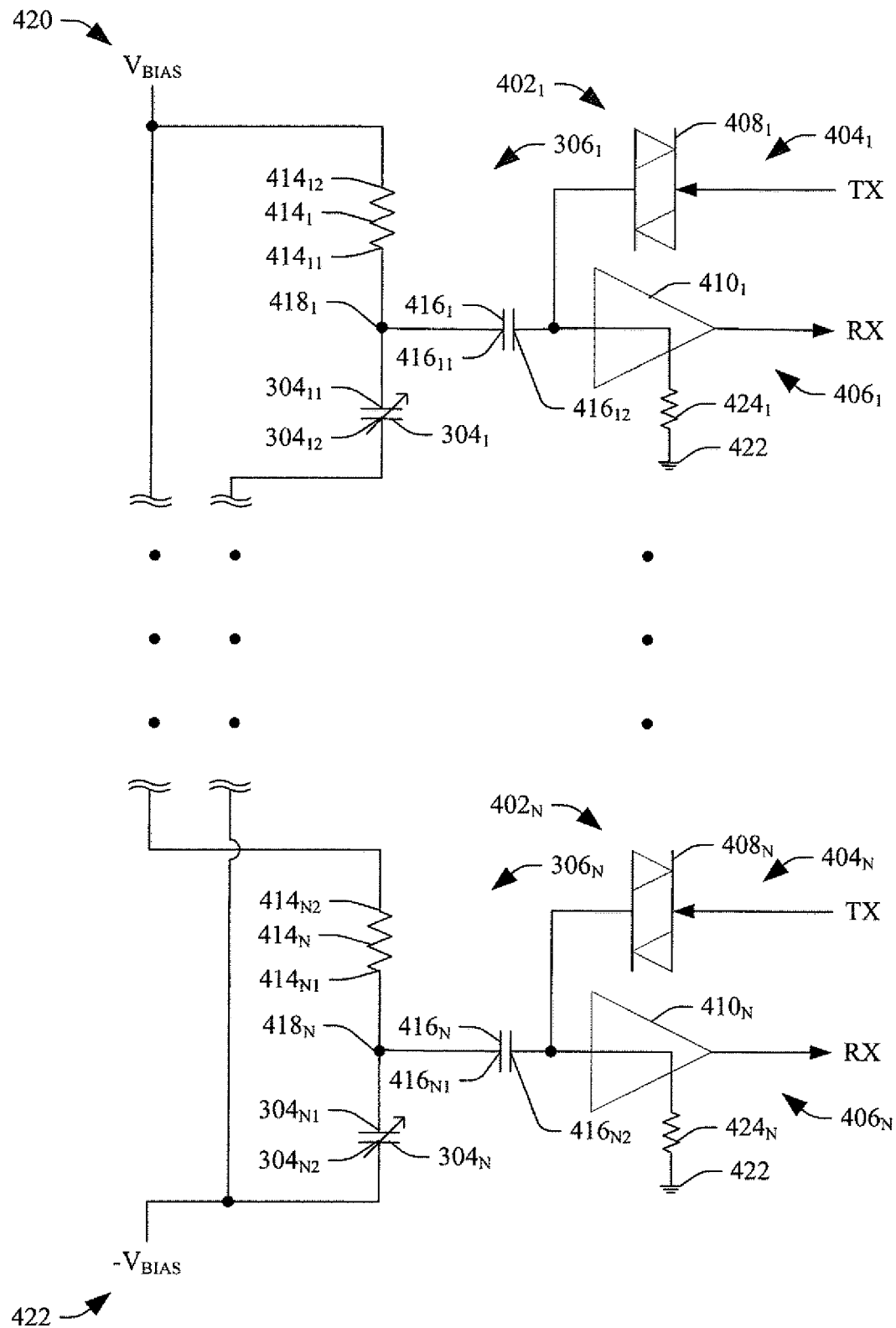
FIG. 4 schematically illustrates an example of the CMUT element bias network.

FIG. 4 illustrates an example of the bias network 306 in connection with the CMUT elements 304. The CMUT elements 304 include N CMUT elements $304_1, \ldots, 304_N$, where N is a positive integer (e.g., 16, 32, 64, 128, 196, 256, etc.). The biasing network 306 include N biasing network $306_1, \ldots, 306_N$. Each of the N biasing network $306_1, \ldots, 306_N$ is associated with a corresponding one of the N CMUT elements $304_1, \ldots, 304_N$. Each of the N CMUT elements $304_1, \ldots, 304_N$ is also associated with corresponding front end electronics $402_1, \ldots, 402_N$.

Each of the front end electronics $402_1, \ldots, 402_N$ includes a transmit channel $404_1, \ldots, 404_N$ and a receive channel $406_1, \ldots, 406_N$. The transmit channel $404_1, \ldots, 404_N$ includes an anti-pole diode $408_1, \ldots, 408_N$. The receive channel $406_1, \ldots, 406_N$ includes an amplifier $410_1, \ldots, 410_N$, which is referenced to ground 422 through resistive element $424_1, \ldots, 424_N$. The bias-network $306_1, \ldots, 306_N$ includes a resistive element $414_1, \ldots, 414_N$ and CMUT elements $304_1, \ldots, 304_N$ and electrically connects the CMUT elements $304_1, \ldots, 304_N$ and the front end electronics $402_1, \ldots, 402_N$. A DC-blocking capacitor $416_1, \ldots, 416_N$ is located between the CMUT element $104_1, \ldots, 104_N$ and both the amplifier $410_1, \ldots, 410_N$ and the anti-pole diode $408_1, 408_N$.

A first end $304_{11}, \ldots, 304_{N1}$ of the CMUT element $304_1, \ldots, 304_N$, a first end $414_{11}, \ldots, 414_{N1}$ of the resistive element $414_1, \ldots, 414_N$, and a first end $416_{11}, \ldots, 416_{N1}$ of capacitive element $416_1, \ldots, 416_N$ are electrically connected at a junction $418_1, \ldots, 418_N$. A second end $414_{12}, \ldots, 414_{N2}$ of the resistive element $414_1, \ldots, 414_N$ is electrically connected to a same first voltage bias ($V_{BIAS}$) 422. A second end $416_{12}, \ldots, 416_{N2}$ of capacitive element $416_1, \ldots, 416_N$ is electrically connected to the amplifier $410_1, \ldots, 410_N$. A second end $304_{12}, \ldots, 304_{N2}$ of the CMUT element $304_1, \ldots, 304_N$ is electrically connected to a same second voltage bias ($-V_{BIAS}$) 422.

The first and second bias voltages 420 and 422 are opposite in polarity. For example, in one instance the first bias voltage ($V_{BIAS}$) 420 has a positive value and the second bias voltage ($V_{BIAS}$) 420 has a negative value. As such, the first and second biases voltage 420 and 422 will apply the total DC voltage differential across the CMUT element $304_{11}, \ldots, 304_{N1}$. The AC voltage at the operating frequency will be applied to the junction $418_1, \ldots, 418_N$ and coupled to the receiver/transmitter path through the capacitor $416_1, \ldots, 416_N$. In a variation, the first voltage bias ($V_{BIAS}$) 420 has a negative voltage and the second voltage bias ($V_{BIAS}$) 422 has a positive voltage. The first and second voltage biases 420 and 422, in one instance, have a same magnitude. In another instance, the magnitude of the first and second voltage biases 420 and 422 is different.

In transmit mode, the anti-pole diode $408_1, \ldots, 408_N$ routes a high voltage transmit pulse from the transmit circuit 308 (FIG. 3), through the bias-network $306_1, \ldots, 306_N$, to the CMUT element $304_1, \ldots, 304_N$. In receive mode, the blocking anti-pole diode $408_1, \ldots, 408_N$ is an open circuit. In receive mode, the signal generated by the CMUT $104_1, \ldots, 104_N$ in response to the CMUT $104_1, \ldots, 104_N$ receiving an echo(s) signal passes through and is amplified by the amplifier $112_1, \ldots, 112_N$ and is routed to the receive circuit 310 (FIG. 3). In a configuration in which $V_{BIAS}$ 420 and $-V_{BIAS}$ 422 are equal in magnitude and opposite in polarity, the voltage "V" at the junction $418_1, \ldots, 418_N$ is $2*V_{BIAS}$.

Generally, "V" can be any voltage between $V_{BIAS}$ and $2*V_{BIAS}$, or $V_{BIAS} \leq V \leq 2*V_{BIAS}$, depending on the value of $-V_{BIAS}$ 422. The second bias voltage ($-V_{BIAS}$) 422 can be driven for the entire range of $V_{BIAS} \leq V \leq 2*V_{BIAS}$ with the resistive element $414_1, \ldots, 414_N$ and the capacitive element $416_1, \ldots, 416_N$ rated for the first bias voltage ($V_{BIAS}$) 420. Thus, e.g., the bias voltage can be doubled (e.g., to $2*V_{BIAS}$) with the same electrically rated bias network $306_1, \ldots, 306_N$ (e.g., the bias network $306_1, \ldots, 306_N$ rated for $V_{BIAS}$). This allows for increasing the sensitivity/efficiency for both transmit and receive. For example, in one non-limiting instance, increasing the bias voltage from $V_{Bus}$ to $2*V_{Bus}$ can lead to an increase in sensitivity on an order of ten decibels (10 dB) to fifteen decibels (15 dB), such as eleven (11 dB), twelve (12 dB), thirteen (13 dB), etc. decibels, or more.

Furthermore, should a single CMUT element 304 (e.g., CMUT $304_1$) fail through an electrical short, the failure is limited to the single CMUT element 304 (e.g., CMUT $304_1$). The only component subject to a full bias voltage is a CMUT element 304 itself (e.g., CMUT $304_1$). With a feasible rating, e.g., of 600 V DC, this is not a problem with present technology. In case of a fault in a CMUT element 304 (e.g., CMUT $304_1$), the resistive element $414_1, \ldots, 414_N$ (e.g., resistive element $414_1$) will be subjected to the voltage $2*V_{BIAS}$. In this exceeds the rating of the resistive element $414_1, \ldots, 414_N$, e.g., where the resistive element $414_1$ is a surface mount, film-type resistor, the resistive element $414_1$ will fail to an open circuit.

In one instance, the controller 322 controls at least one of the first bias voltage ($V_{BIAS}$) 420 or the second bias voltage ($-V_{BIAS}$) 422. For example, the apparatus 300 may include a set of default scanning modes, each with a different sensitivity, which is driven by a fixed first bias voltage ($V_{BIAS}$) 420 and variable second bias voltage ($-V_{BIAS}$) 422. In response to a user providing a mode selection input via the user interface 324, the controller 322 determines the corresponding second bias voltage ($-V_{BIAS}$) 422 to apply (e.g., via a look up table (LUT) or otherwise) and controls the bias network 306 to apply the appropriate first and second bias voltages 420 and 422.

In another instance, the user can use the user interface 324 to change the sensitivity during a scan. For this, the user may select a sensitivity from a predetermined set of sensitivities, invoke a control that increases and decreases the sensitivity until a desired sensitivity is reached, etc. In any case, the controller 322 determines the corresponding second bias voltage ($-V_{BIAS}$) 422 to apply and controls the bias network 306 to apply the appropriate first and second bias voltages 420 and 422. In one non-limiting example $V_{BIAS}$ can be any voltage within a range of 80 V to 250 V or −80 V to −250 V. For example, in one instance, $V_{BIAS}$=90 V and $-V_{BIAS}$=−90 V, or $V_{BIAS}$=−90 V and $-V_{BIAS}$=90 V. Other voltages are contemplated herein.

In another instance, the second bias ($-V_{BIAS}$) 422 is adjusted to accommodate several different probe types, where the CMUT transducer array elements 304 have a different maximum allowable $V_{BIAS}$. In this situation, the controller 322 would read information about the maximum $V_{BIAS}$ from a given probe 602 and adjust the second bias ($-V_{BIAS}$) 422 for that probe accordingly.

Figure 5:
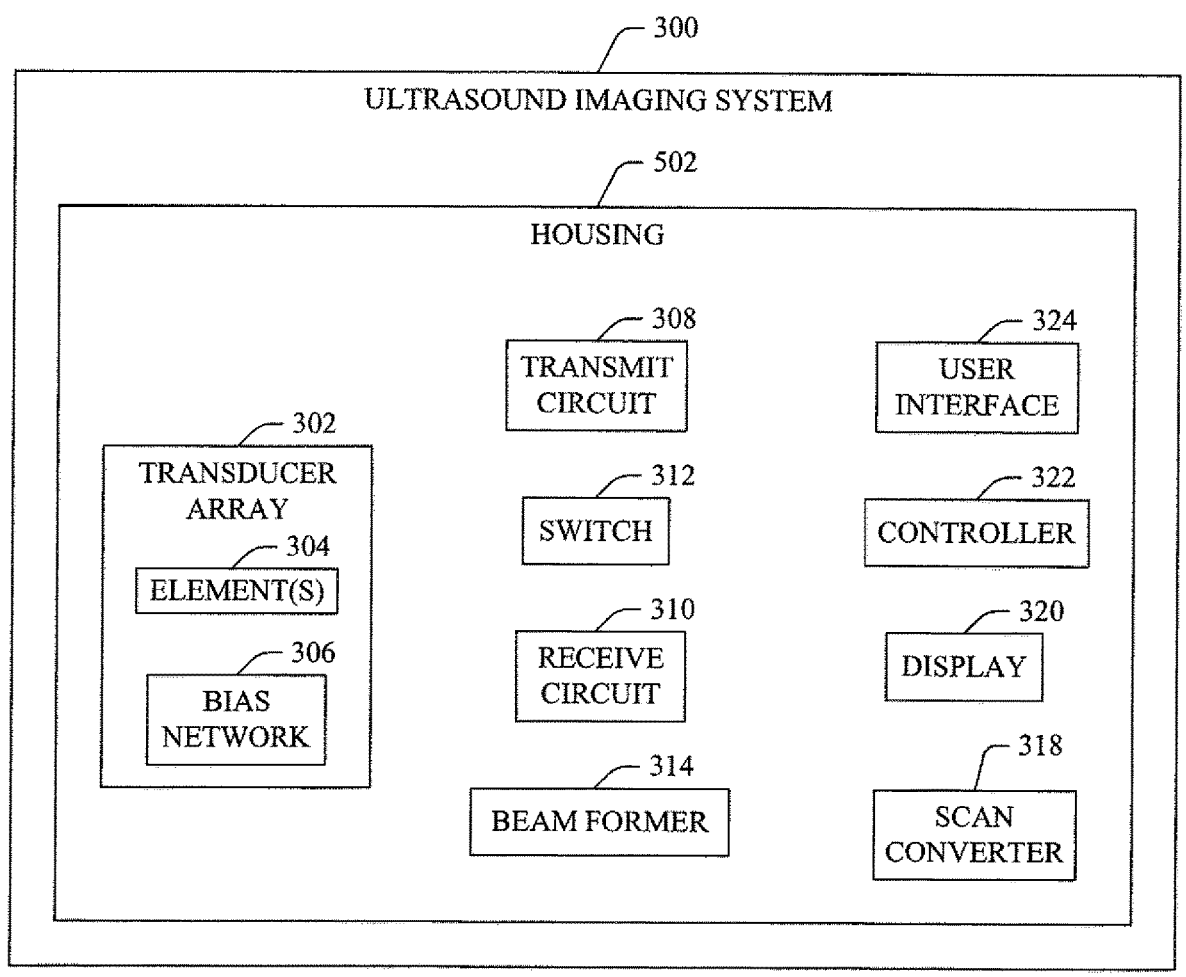
FIG. 5 schematically illustrates an example of the ultrasound imaging system.

In FIG. 5, the apparatus 300 is included in a hand-held device with a single enclosure or housing 502, which houses and/or physically supports the transducer array 304, the transducer elements 304, the bias network 306, the transmit circuitry 308, the receive circuitry 310, the switch 312, the beamformer 314, the scan converter 318, the display 320, the controller 322, and the user interface 324 in the system 402. An example of a hand-held device is described in U.S. Pat. No. 7,699,776 to Walker et al., entitled "Intuitive Ultrasonic Imaging System and Related Method Thereof," and filed on Mar. 6, 2003, which is incorporated herein in its entirety by reference. Other hand-held devices are also contemplated herein.

Figure 6:
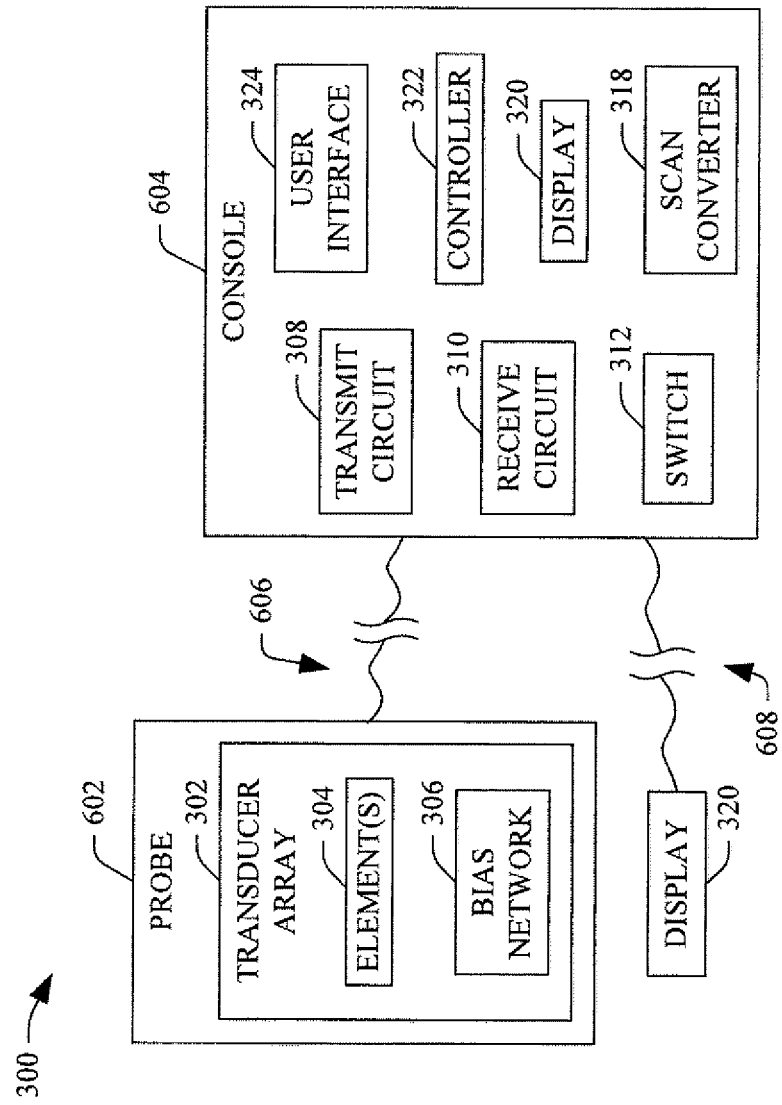
FIG. 6 schematically illustrates another example of the ultrasound imaging system.

In FIG. 6, the ultrasound apparatus 300 includes a console 604 and a separate transducer probe 602 that interfaces therewith via a communication channel 606. The ultrasound transducer probe 602 includes the transducer array 304, the transducer elements 304, and the bias network 306. The console 604 includes the transmit circuitry 308, the receive circuitry 310, the switch 312, the beamformer 314, the scan converter 318, and the user interface 418. The display 320 is shown as a separate from the console 604 and the transducer probe 602 and interfaced with the console 604 via a communication channel 608. In a variation, the ultrasound transducer probe 602 is additionally or alternatively part of the console 604.

Figure 7:
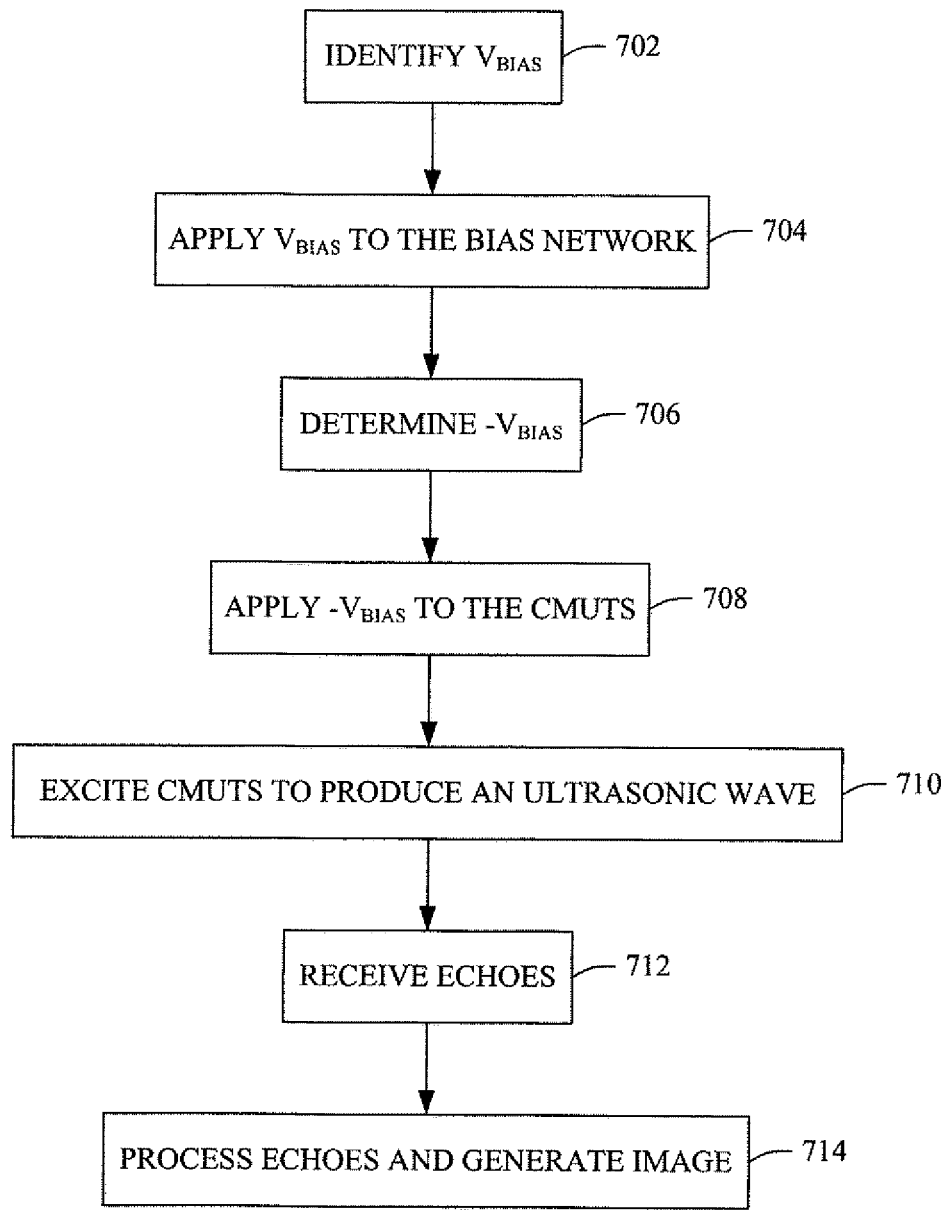
FIG. 7 illustrates an example method in accordance with the embodiments described herein.

FIG. 7 illustrates an example method in accordance with the embodiments described herein.

It is to be appreciated that the order of the following acts is provided for explanatory purposes and is not limiting. As such, one or more of the following acts may occur in a different order. Furthermore, one or more of the following acts may be omitted and/or one or more additional acts may be added.

At 702, identify a CMUT sensitivity of interest for the transducer array 302 for a scan.

At 704, apply the first bias voltage ($V_{BIAS}$) 420 to the bias network 306.

At 706, determine a value of the second bias second bias voltage ($-V_{BIAS}$) 422 based on the sensitivity of interest and the first bias voltage ($V_{BIAS}$) 420.

At 708, apply the second bias second bias voltage ($-V_{BIAS}$) 422 420 to the CMUT elements 304.

At 710, excite at least a sub-set of the CMUT elements 304 to produce an ultrasonic wave that traverses a field of view.

At 712, receive, with at least a sub-set of the CMUT elements 304, echoes produced in response to an interaction of the ultrasonic wave with structure in the field of view.

At 714, generate an image of the structure by processing the echoes.

It is to be appreciated that the methods herein may be implemented by one or more processors executing computer executable instructions stored, encoded, embodied, etc. on computer readable storage medium such as computer memory, non-transitory storage, etc. In another instance, the computer executable instructions are additionally or alternatively stored in transitory or signal medium.

It is to be understood that the terms "first", "second" and so forth as used herein refer to an order in which an element is introduced. For example, a "first" end is an end introduced before another end, which, if introduced next, is referred to as a "second end". If such elements were introduced in the opposite order, the "second" end would be the "first" end. Furthermore, the terms "first", "second", and so forth do not represent a temporal characteristic of the elements described herein.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An apparatus, comprising:
   a transducer array, including:
   a plurality of CMUT elements, each with a first end and a second end; and
   a bias network that is electrically connected with the first and second ends of the plurality of CMUT elements,
   wherein the bias network applies a first bias voltage to the first end of the plurality of CMUT elements and a second bias voltage to the second end of the plurality of CMUT elements, and the first and second bias voltages bias the plurality of CMUT elements.

2. The apparatus of claim 1, wherein the first bias voltage and the second bias voltage have a same magnitude but opposite polarity.

3. The apparatus of claim 1, wherein the first bias voltage and the second bias voltage have a different magnitude and opposite polarity.

4. The apparatus of claim 1, the bias network including:
   a plurality of resistive elements, each having a first end and a second end; and
   a plurality of capacitive elements, each having a first end and a second end,
   wherein the first end of the plurality of resistive elements is in electrical communication with the first end of the plurality of capacitive elements and the second end of the plurality of CMUT elements, and the first bias voltage is applied to the second end of the plurality of resistive elements.

5. The apparatus of claim 4, wherein the plurality of resistive elements and the plurality of capacitive elements have an electrical rating corresponding to the first bias voltage and not a summation of the first bias voltage and the second first bias voltage.

6. The apparatus of claim 4, further comprising:
   a transmit channel electrically connected to the second end of the plurality of capacitive elements; and
   a receive channel electrically connected to the second end of the plurality of capacitive elements.

7. The apparatus of claim 1, wherein the first end of the plurality of CMUT elements or the second end of the plurality of CMUT elements is electrical ground.

8. The apparatus of claim 7, wherein the bias voltage of the first or second bias voltage applied to the electrical ground is at least one and a half times larger than the other of the bias voltage of the first or second bias voltage.

9. The apparatus of claim 6, further comprising:
   a transmit circuit selectably in electrical communication with the transmit channel;
   a receive circuit selectably in electrical communication with the receive channel; and
   a switch that switches between the transmit circuit and the receive circuit respectively for transmit and receives operations.

10. The apparatus of claim 1, further comprising:
    a controller that controls at least one of a value of the first bias voltage and a value of the second bias voltage.

11. The apparatus of claim 10, wherein the value of the first bias voltage is a fixed value, and the controller controls the value of the second bias voltage based on a sensitivity of interests of the transducer array.

12. The apparatus of claim 11, wherein the controller receives a first signal indicative a user selected sensitivity of interests.

13. The apparatus of claim 10, wherein the controller receives a second signal indicative of a different sensitivity of interests, and the controller controls the value of the second bias voltage based on the different sensitivity of interests.

14. A method, comprising:
    biasing, with bias network, a CMUT element of an transducer array using a bipolar signal that concurrently applies a first bias voltage and a second bias voltage across the CMUT element;
    transmitting, by a transmit circuit, an excitation signal to the CMUT element; and
    receiving, by a receive circuit, an echo signal from the CMUT element.

15. The method of claim 14, where the first bias voltage and the second bias voltage have a same magnitude but opposite polarity.

16. The method of claim 14, further comprising:
    determining a value of one of the first or second bias voltages based on a sensitivity of interest for the CMUT element; and
    controlling the one of the first or second bias voltages based on the determined value.

17. The method of claim 16, further comprising:
    obtaining a different sensitivity of interest for the CMUT element; and
    changing the value of the one of the first or second bias voltages based on the different sensitivity of interest for the CMUT element.

18. The method of claim 14, further comprising:
    applying the same bipolar signal for both transmit and receive operations of the transducer array.

19. The method of claim 14, further comprising:
    applying the first bias voltage to a first terminal of the CMUT element; and
    applying the second bias voltage to a second terminal of the CMUT element, wherein one of the first or second terminals is an electrical common terminal of the CMUT element.

20. An ultrasound imaging system, comprising:
    at least one transducer element;
    a bias network of the at least one transducer element, wherein the bias network is configured to provide bipolar biasing for the at least one transducer element through concurrently biasing both ends of the at least one transducer element.

* * * * *